United States Patent [19]

Freilich

[11] Patent Number: 4,591,793
[45] Date of Patent: May 27, 1986

[54] AGGREGOMETER ELECTRODE STRUCTURES

[76] Inventor: Arthur H. Freilich, 2025 Olcott Ave., Ardmore, Pa. 19003

[21] Appl. No.: 620,503

[22] Filed: Jun. 14, 1984

[51] Int. Cl.⁴ ............................................. G01N 27/07
[52] U.S. Cl. ...................................... 324/446; 422/73; 324/65 P
[58] Field of Search ............... 324/446, 439, 449, 450, 324/71.1, 65 P, 65 R; 422/73; 128/DIG. 22; 73/64.1; 204/426, 430

[56] References Cited

U.S. PATENT DOCUMENTS

| | | | |
|---|---|---|---|
| 4,123,701 | 10/1978 | Josefsen et al. | 324/65 R |
| 4,301,414 | 11/1981 | Hill et al. | 324/446 |
| 4,319,194 | 3/1982 | Cardinal et al. | 324/449 |

*Primary Examiner*—Reinhard J. Eisenzopf
*Assistant Examiner*—Kevin D. O'Shea
*Attorney, Agent, or Firm*—Walter B. Udell

[57] ABSTRACT

A disposable low cost electrode structure for measuring platelet aggregation in whole blood or PRP which utilizes conductive ink or foil for the electrodes with the electrode pattern printed, heat-stamped or silk-screened onto a suitable plastic non-reactive base. The base material can be any material which does not react with blood and is stiff enough, for example a polycarbonate, while the conductive element can be made with a silver conductive ink. The electrodes can be on one or both sides of the base or substrate material. Platelet aggregates start and build up on the leading edge of a narrow body inserted into the flow path of the blood. The conductive pattern must have its active element on or very near the leading edge of the electrode base material, and in contact with the blood, and the non-active areas of the conductive pattern must be insulated electrically from the blood or plasma being tested so as to allow sensing of the change in resistance caused by the platelet build-up on the active area. Tests of material thicknesses at stirring rates and in configurations that are used for aggregation indicate that the platelets will build up on physical thicknesses ranging from less than 0.005 inches up to about 0.025 inches. Above that, the platelets, which average in diameter about 2 to 3 microns, do not accumulate on the edge. The electrodes should have a means for making connection to the measuring circuit which will sense platelet aggregation by measuring the increase of resistance between the two legs of the electrode assembly.

20 Claims, 19 Drawing Figures

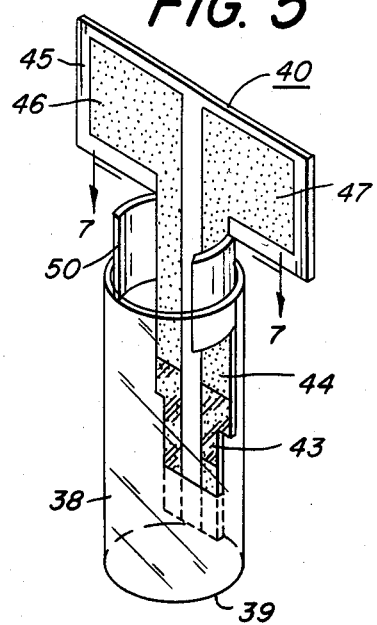
FIG. 5
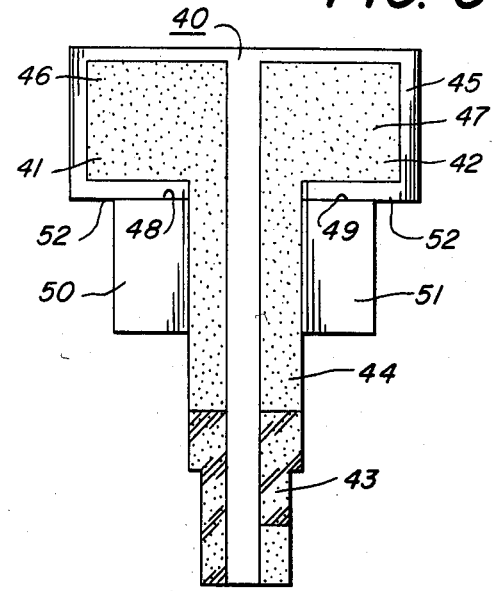
FIG. 6
FIG. 8A
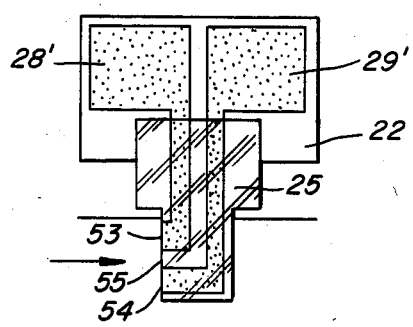
FIG. 8B
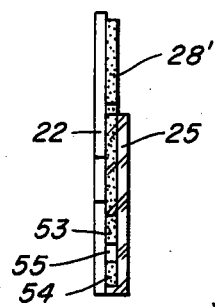
FIG. 7
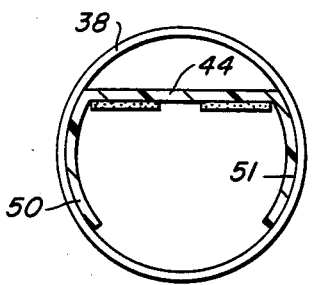
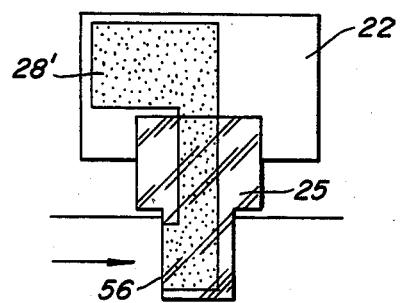
FIG. 9A
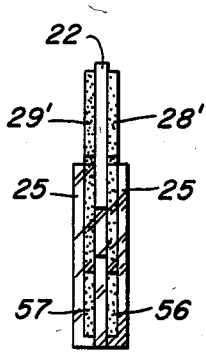
FIG. 9B

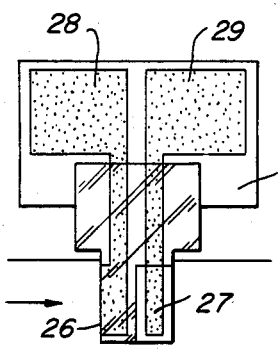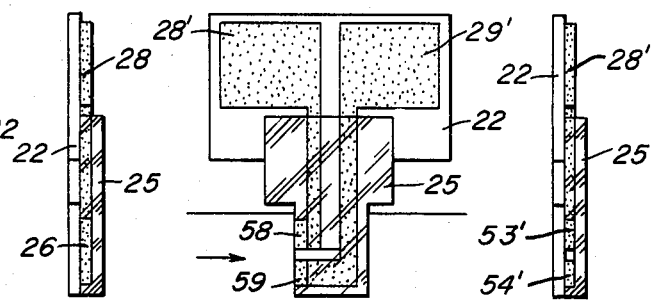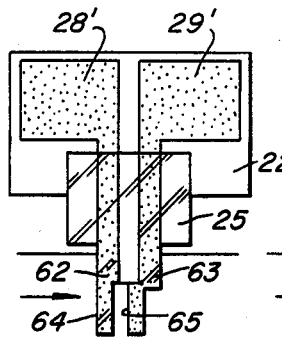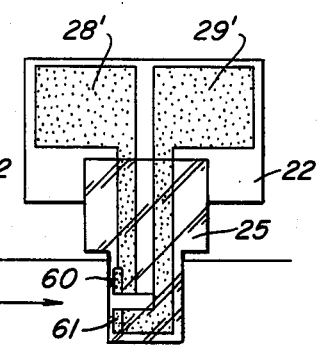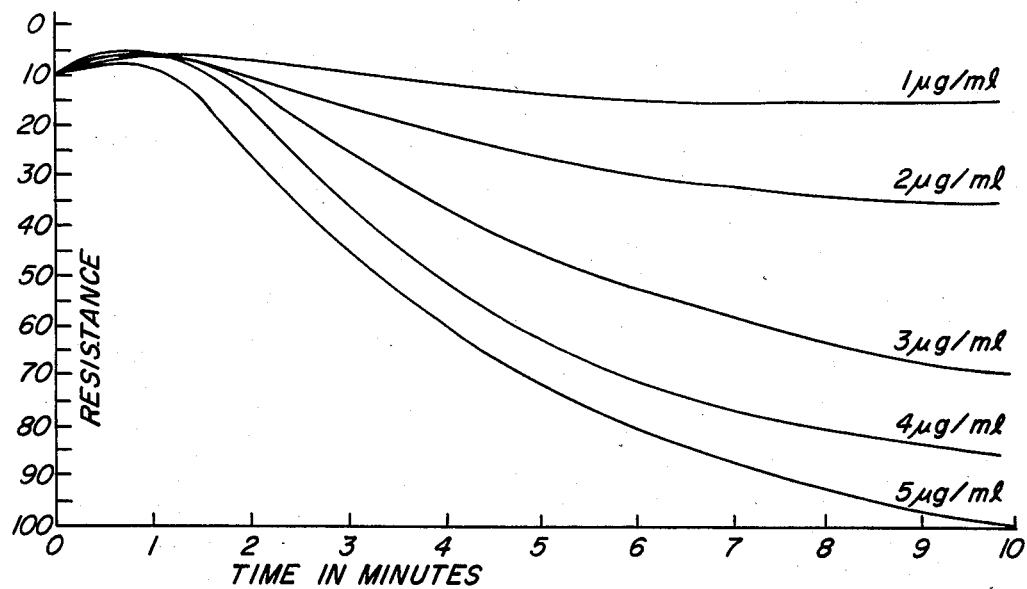

AGGREGOMETER ELECTRODE STRUCTURES

This invention relates to electrode structures for use in conjunction with instruments known as aggregometers for detecting platelet aggregation in whole blood.

BACKGROUND OF THE INVENTION

Aggregometers detect platelet aggregation in whole blood by passing a very small electric current between two electrodes immersed in a sample of blood or PRP (platelet rich plasma) and measuring the electrical impedance between the electrodes. During initial contact with the blood or PRP, the electrodes become coated with a monolayer of platelets. When an aggregating agent is added, platelets gradually accumulate on the monolayer coating, increasing the impedance between the electrodes. The change in impedance is recorded as a function of time on a strip chart recorder.

It is important to distinguish between platelet aggregation and clotting because the electrode structure devices which have in the past been developed for measuring clotting times are not operative for detecting and measuring platelet aggregation. Aggregation and clotting are two distinctly different hematological phenomena, and the differences are described in Chapter 1 of "Hemorrhage and Thrombosis" by Drs. Salzmann and Britten. In essence, platelet aggregation occurs during primary hemostasis, while clotting occurs during secondary hemostasis. It is stated that platelet aggregation in response to pharmacologically active substances such as ADP is largely independent of blood coagulation or clotting. The essential part of coagulation is the conversion of a soluble protein, fibrinogen, into an insoluble network of fibers, fibrin. In a time sense, the process of platelet aggregation is complete before coagulation or clotting has occurred. Typical of devices for measuring clotting times are the Rosenthal, U.S. Pat. No. 2,555,937, and to Stoner U.S. Pat. No. 3,840,806. These devices will not measure platelet aggregation.

A suitable electrode structure for the purpose of measuring platelet aggregation has been developed by Cardinal and Flower and is disclosed in U.S. Pat. No. 4,319,194. This patent covers specifically an electrode for measuring platelet aggregation in whole blood or PRP, using a wire electrode, and has eliminated the need for centrifuging blood to obtain PRP and PPP (platelet poor plasma.) and then using these plasmas to measure aggregation of platelets optically. The ability to speed up the tests, reduce labor costs, and test the platelets in their natural milieu was an important advance in platelet studies. The measurement in whole blood also allows studies to be performed in cases where optical aggregation does not work, such as with giant platelets (Bernard-Soulier syndrome), where red cells have been lysed or where it is impossible to obtain enough blood to make PRP and PPP, such as with small animals or babies. However, the use of a wire electrode as taught in the Cardinal and Flower patent has disadvantages. As a first matter, although precious metal electrodes are superior to base metals since base metals drift in blood/saline mixtures, precious metal electrodes are expensive. Moreover, any electrode made with wires requires expensive handling of individual electrode assemblies and parts during fabrication, whether the electrodes are made by insertion molding, hand fabrication or machine fabrication.

Accordingly, there is a need for a disposable platelet aggregation measuring system in which the items in contact with the sample, such as the cuvette. the electrode and the stirring agitator, are thrown away after a single use, particularly in clinical applications. This need is due to the fact that the doctor or medical technician doing the test is handling blood or plasma from patients or animals and is therefore exposed to diseases transmitted through these fluids. With a "single use" disposable system, it is not necessary to retrieve, cleanse and re-use the electrode assembly and/or other items such as the stir bar that have been in contact with the blood.

This problem has always existed, as for example with regard to hepatitis which has long been recognized as a danger to the doctor or technician. More recently the problem has been severely exacerbated by the presently accepted theory that AIDS is transmitted via body fluids. At present, AIDS is a fatal, incurable and non-preventable disease. Therefore, there is even greater reluctance on the part of the medical profession to handle blood where not necessary.

SUMMARY OF THE INVENTION

A disposable aggregation system requires a single-use electrode assembly that can be mass produced at low cost. The precious metal electrode now in use is priced at about $95.00. Obviously, it is not economically feasible to throw it away after each test. The electrode structures according to the invention provide electrode assemblies using ink or foil as the conductive element with the electrode pattern printed, heat-stamped or silk-screened onto a suitable plastic, non-reactive base. The base material can be any material which does not react with blood and is stiff enough, for example a polycarbonate, while the conductive elements can be made with a silver conductive ink.

Different approaches to suitable electrode designs have led to the key observation that the platelet aggregates build up on the leading edge of a narrow body inserted into the flow path of the blood. While some of the platelet mass may slough over onto the flat surfaces as the mass builds up, the platelet buildup starts on the leading edge and grows up on that edge.

Tests of various thicknesses of material at stirring rates and in configurations that are used for aggregation indicate that the platelets will build up on physical thicknesses ranging from less than 0.005 inches up to about 0.025 inches. Above that, the platelets, which average in diameter about 2 to 3 microns, do not accumulate on the edge. Since the lower limit is determined by how thick the base material must be to remain rigid in the flow path, thicknesses less than approximately 0.005 inches were not usable. This thickness range is broader than that described by Cardinal and Flowers in their patent, i.e. a wire diameter of 0.25 mm or 0.01" maximum. The thickness at present found to be best with the materials being worked with is 0.015" or about 0.36 mm. However, it is not the wire (rod) configuration that matters, it is the cross sectional width of the leading edge.

The disposable electrode can be made in many different configurations. The essential factors are:

1. A conductive pattern produced on a base of sufficient rigidity to remain stable in the flow path.

2. The conductive pattern must be of a material which is non-reactive with blood, and minimally reactive with saline to prevent drift.

3. The base material must be non-reactive with blood and platelets; most plastics fit this category.

4. The conductive pattern must have its active element on or very near the leading edge of the electrode base material, and in contact with the blood.

5. The non-active areas of the conductive pattern must be insulated electrically from the blood or plasma being tested so as to allow sensing of the change in resistance caused by the platelet build-up on the active area.

6. The overall thickness of the base material, the conductive active area and the insulating layer(s) must not exceed the width which would prevent platelets from collecting; an overall width of about 0.010 to 0.015 inches works well under normal flow rate conditions providing a rigid structure for the electrode while being well within the 0.025 maximum width.

7. The assembly must be capable of being mass-produced at low cost.

8. The electrode should have a means for making connection to the measuring circuit which will sense platelet aggregation by measuring the increase of resistance between the two legs of the electrode assembly.

9. The electrode assembly should mount easily in an inexpensive non-reactive cuvette.

Suitable electrode configurations include silk-screened patterns using conductive inks, preferably silver inks which are resistant to corrosion in the fluid; heat-stamped patterns; or printed patterns. Suitable electrodes can also be made by laminating conductive foil, separated and insulated by laminations of plastic. However, the expense of laminating this assembly is relatively high so that from an economic standpoint, it is not the preferred method. The electrodes can be single sided or double sided. The single sided patterns will normally be less expensive to manufacture and are therefore preferable.

The number of active electrode surfaces can be one or more, where "active" is defined as the surface on which platelet aggregates build up. Since the active surfaces are small, the electrical resistance is high. By making one electrode active and the other simply a large, flat surface which conducts current but which does not support platelet buildup, the overall resistance of the circuit is reduced. However, the sensitivity is also reduced since only the active electrode surface changes resistance as the platelets accumulate. With two active surfaces, the sensitivity is very high since the entire conductive area is subject to platelet build-up and therefore the change in resistance is large.

A primary object of the invention is to provide a novel platelet aggregation electrode assembly sufficiently inexpensive in cost that it may be a single-use disposable item.

Another object of the invention is to provide a novel disposable platelet aggregation electrode assembly as aforesaid comprising an electrically non-conductive and blood non-reactive substrate having a pair of electrically conductive spaced apart electrodes adhered to the substrate for partial immersion in a platelet carrying medium.

Another object of the invention is to provide a novel disposable platelet aggregation electrode assembly as aforesaid wherein selected areas of the electrically conductive electrodes are exposed for contact with the medium, and the remaining areas disposed within the medium are electrically insulated therefrom.

A further object of the invention is to provide a novel disposable platelet aggregation electrode assembly as aforesaid having a total thickness in one dimension in the range between approximately 0.005 inches and 0.025 inches.

Yet another object of the invention is to provide a novel disposable platelet aggregation assembly as aforesaid wherein the electrode assembly substrate is a plastic material, and wherein the electrodes on the substrate are made from a silver conductive ink.

A still further object of the invention is to provide a novel disposable platelet aggregation electrode assembly as aforesaid which is used in conjunction with an inexpensive disposable cuvette made of blood non-reactive material.

The foregoing and other objects of the invention will become clear from a reading of the following specification in conjunction with an examination of the appended drawings, wherein.

Figure 1:
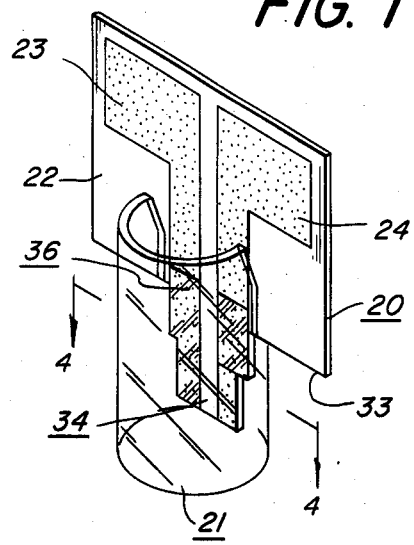
FIG. 1 is an isometric view of one form of the invention showing an electrode configuration on a substrate disposed in a cuvette.
Figure 3:
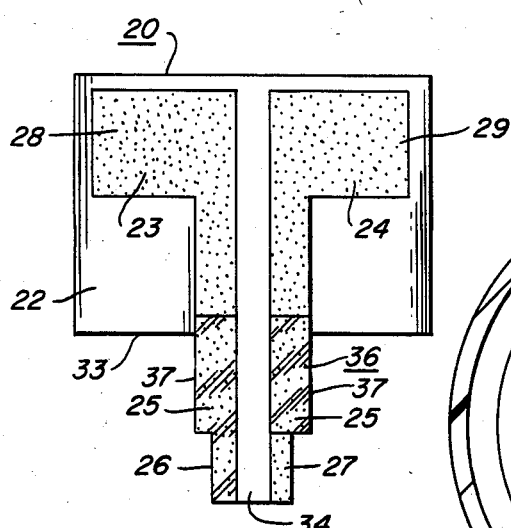
FIG. 3 is a front elevation on an enlarged scale of the electrode assembly shown in FIG. 1.
Figure 4:
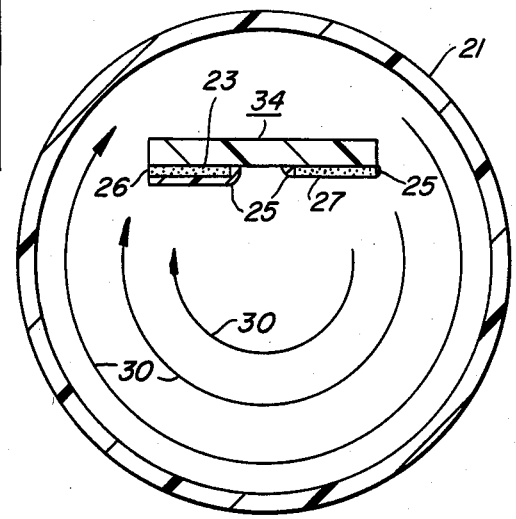

FIG. 4.is a horizontal section on an enlarged scale through the assembly of FIG. 1 as would be seen when viewed along line 4—4 thereof;

FIG. 5 is an isometric view of another form of the invention showing a different electrode substrate configuration and a different cuvette;

FIG. 6 is a front elevation on an enlarged scale of the electrode assembly shown in FIG. 5;

FIG. 7 is a horizontal section on an enlarged scale through the assembly of FIG. 5 as would be seen when viewed along line 7—7 thereof;

FIGS. 8A through 13 show different embodiments of electrode configurations on the same general substrate shape as that shown in the embodiment of FIG. 1, although such electrode configurations may be as readily utilized on substrates as shown in FIG. 5; and FIG. 14 is a graph showing dose response curves obtained with an electrode structure of the type shown in FIGS. 3, 10A and 10B.

In the several figures, like elements are denoted by like reference characters.

Considering now the figures, and first FIGS. 1 to 4, there is seen an electrode/cuvette assembly including the electrode assembly designated generally as 20 and the cuvette designated generally as 21. As best seen in FIG. 3, the electrode assembly includes the generally T-shaped substrate 22 onto which is silk screened or otherwise adhered a pair of conductive electrodes 23 and 24 of generally inverted-L shape, the lower ends of which are selectively coated with an insulating material 25. As best seen in the showing of FIG. 4, the insulating material 25 is not present at the left hand edge of electrode 23 to leave an exposed edge 26, and the insulating material 25 similarly stops short of the front face 27 of the lower edge of electrode 24. The upper ends 28 and 29 respectively of electrodes 23 and 24 are not insulated so that they may be connected to a source of electricity supplied by the aggregometer instrument with which the electrode structure is utilized. When the electrodes are so connected, the exposed edges 26 and 27 respectively on electrodes 23 and 24 become the electrically active areas, the remaining portions of the electrode surfaces which are immersed in the medium being not electrically active by reason of their electrical isolation from the medium by the intervening insulating material 25.

As best seen in FIG. 4 by the arrows 30, the medium in the cuvette 21 is stirred to produce movement in the direction shown by the arrows by means of a stirring rod, not shown, but which is conventional in the art and forms no part of the invention. The exposed surface 26 of electrode 23 is the "active" surface as previously defined on which the platelet aggregates build up, the surface 27 being a relatively large flat surface which conducts current but does not support platelet build-up.

The cuvette 21 is provided with a vertical slot 31 formed along a chord of the circular cross section of the cuvette which is spaced approximately half the radius from the center of the cuvette, and is also provided with a guide-in truncation 32 to assist in placing the electrode structure properly down into the cuvette. The lower edge 33 of the substrate 22 is so dimensioned with respect to the overall height of the electrode assembly and the cuvette 21 that when the lower edge 33 is seated in the cuvette at the bottom of the slot 31, the active tail 34 of the electrode assembly is submerged in the fluid medium with its lower edge spaced above the base 35 of the cuvette. The width of the tail section 34 of the electrode assembly, as best seen in FIG. 4, is sufficiently narrow to allow free movement of the fluid medium in the cuvette in front of and behind the tail.

The intermediate section 36 of the electrode assembly 20 is of a width such that it is equal to the chord length of the cuvette cross-section at the half radius point so that the side edges 37 engage the inside wall of the cuvette at the chordal points to mechanically stabilize the electrode assembly. The same basic substrate shape is shown in the electrodes illustrated in FIGS. 8 through 13, although the electrode configurations are somewhat different, as will be subsequently described.

Figure 2:
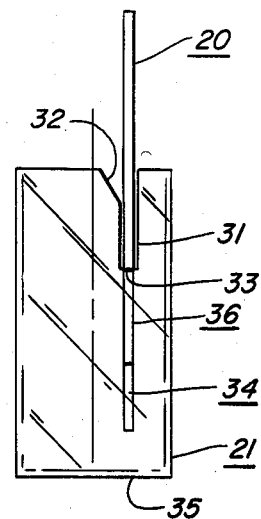
FIG. 2 is a side elevation of the configuration shown in FIG. 1.

A second embodiment of the invention is illustrated in FIGS. 5, 6 and 7 and utilizes a modified substrate shape in order to avoid the necessity of a special cuvette of the type 21 shown in FIGS. 1 and 2. In FIGS. 5 and 7 it is observed that the cuvette 38 is an open-topped cylindrical cuvette having a bottom wall 39 and no slot arrangement comparable to slot 31 in cuvette 21. This is a much less expensive device to make, but requires modification of the substrate in order to provide a different form of mechanical stabilization. This is accomplished in the electrode assembly shown in FIGS. 5 and 6. In the embodiment of FIG. 6, the electrode assembly 40 again has a pair of electrodes 41 and 42 of inverted-L shape, has an active tail section 43 and an intermediate section 44 which function in the same manner as already described for the tail section 34 and intermediate section 36 of the electrode assembly 20 shown in FIG. 1.

The electrode assembly 40 differs from the electrode assembly 20 basically in that the portion of the substrate 45 immediately below the electrodes contact areas 46 and 47 is slit along the lines 48 and 49 to form a pair of wings 50 and 51 which are resiliently foldable forward as shown in FIG. 5 and in FIG. 7 to hold the electrode assembly 40 stably in place in the cuvette 38. As shown in FIG. 5 for clarity, the electrode assembly 40 has not been placed completely downward into the cuvette as it would be in normal use. When pressed downward so that the under edges 52 of the substrate above the wings 50 seat downward on the upper edge of the cuvette, the active tail section 43 moves downward into the dotted position shown in FIG. 5. As best seen in FIGS. 7, the wings 50 resiliently bias the electrode assembly radially outward so that the intermediate section 44 positionally stabilizes the electrode assembly in exactly the same manner as in the embodiment shown in FIG. 1.

Although the electrode structures now to be described in connection with the showings of FIGS. 3 and 8A through 13 are all illustrated in connection with the substrate form 22 shown in FIG. 1, it is to be understood that all of these electrode configurations are equally usable with the form of substrate shown as 45 in FIGS. 5 and 6. In all of these forms of electrode assembly, except for the electrically conductive active parts of the electrodes immersed in the medium, it should be understood that the electrically insulating overlay material which overlays the conductive portions of the electrodes covers all of the non-active portions of the electrodes which are below the liquid level and also extends above the liquid level in order to eliminate changes in resistance which could be caused by movement of the meniscus fluid medium being stirred in the cuvette.

In FIGS. 8A through 13, common numbers will be used for the same element, as for example all of the substrates will be designated by the number 22 while the overlying insulation will be designated as 25, and the electrode structures generally will be designated in the contact areas as 28' and 29' with the electrode active regions in the active tail being given specific reference characters to distinguish one from another.

The electrode structure shown in FIGS. 8A and 8B is a one sided pattern with two active electrodes on the substrate 22 and the insulating overlay 25 completely covering the front planar surface of the electrodes except for the contact areas 28' and 29'. Both of the electrodes extend vertically downward from the contact areas 28' and 29' and make a right angled turn to the left terminating in a pair of active edge areas 53 and 54 spaced vertically one below the other and separated by a gap 55. The edge areas 53 and 54 are both sufficiently small that they are "active" edge areas, and both contribute to the change in resistance during aggregation. This configuration has been tested with gap spacings which vary in the range between 1/64 of an inch and 5/32 of an inch, a range of ten to one, and the response curves generated are very close to one another so that it has been determined that this configuration is relatively non-sensitive to the inter-electrode active area spacing within reasonable limits. This provides some latitude for manufacturing tolerances.

The electrode structure shown in FIGS. 9A and 9B are similar to that of FIGS. 8A and 8B in that there are two active edge areas 56 and 57 but they are placed on opposite side faces of the substrate 22 instead of being co-planar as in the structure of FIGS. 8A and 8B. The configuration shown in FIGS. 10A and 10B are exactly the same as that previously described in connection with the showing of FIGS. 1 and 3.

FIGS. 11A and 11B are similar to the showings of FIGS. 8A and 8B excepting that the active edge areas 53 and 54 in the showings of FIG. 8A and 8B, designated in FIGS. 11A and 11B as 53' and 54'are carried to some extent around onto the flat front face of the electrode assembly to include the exposed areas 58 and 59. Platelets will slough over onto these latter surfaces after the mass builds up on the edge and will give a change in resistance. FIGS. 12A and 12B are similar to those of FIGS. 11A and 11B in that they have active areas on the flat faces of the electrodes designated as 60 and 61, but differ from those of FIGS. 11A and 11B in that there are no active edge areas.

FIG. 13 shows a bifurcated active tail region of the electrode assembly having a pair of depending legs 62 and 63 which respectively have active edge areas 64 and 65, the front faces of the depending legs 62 and 63 being completely covered with the insulating material, as are the trailing edges of the legs. Other configurations are also possible, for example using serrated active edge areas to increase the active edge area without substantially increasing the linear length.

FIG. 14 illustrates dose response curves obtained with an electrode structure similar to that shown in FIGS. 3 and 10. These curves, as shown, are for aggregating agent additions of one to five micrograms per milliliter of collagen in normal whole blood, and show the relative change in resistance as a function of time. The curves are similar to those obtained by using the Cardinal-Flower whole blood electrode. The differing response for different doses of aggregating reagent is clearly evident.

Having now described the invention in connection with particularly illustrated embodiments thereof, it will be appreciated that variations and modifications thereof may now naturally occur to those persons normally skilled in the art without departing from the essential scope or spirit of the invention, and accordingly it is intended to claim the same broadly as well as specifically as indicated by the appended claims.

I claim:

1. A platelet aggregation eectrode assembly comprising in combination,
   (a) an electrically non-conductive and blood non-reactive substrate for supporting a pair of electrodes,
   (b) a pair of first and second electrically conductive spaced apart electrodes adhered to and extending for a distance along said substrate, said electrodes each having a first conductive region for electrical connection to a measuring circuit, and each having a second conductive region for immersion in a platelet carrying medium, said first and second conductive regions of each electrode being spaced apart from each other by an intervening length of each said electrode, and
   (c) a layer of electrical insulating material entirely overlying each of said pair of electrodes except at said first and second conductive regions of each said electrode.

2. A platelet aggregation electrode assembly as set forth in claim 1 wherein said substrate, said electrodes and said insulating material form a three dimensional sandwich structure having a total thickness dimension which is small compared to its other two dimensions.

3. A platelet aggregation electrode assembly as set forth in claim 1 wherein the area of said second conductive region of one of said pair of electrodes is much smaller than the area of said second conductive region of the other of said pair of electrodes.

4. A platelet aggregation electrode assembly as set forth in claim 1 wherein said substrate is a substantially planar piece of plastic material.

5. A platelet aggregation electrode assembly as set forth in claim 1 wherein said electrodes on the said substrate are made from a silver conductive ink.

6. A platelet aggregation electrode assembly as set forth in claim 1 wherein said second conductive region of at least one of said pair of electrodes is an "active" surface, where an "active" surface is defined as a surface on which platelet aggregates build up.

7. A platelet aggregation electrode assembly as set forth in claim 1 wherein said second conductive regions of both of said pair of electrodes are "active" surfaces where an "active" surface is defined as a surface on which platelet aggregates build up.

8. A platelet agregation electrode assembly as set forth in claim 1 wherein said second conductive region of one of said pairs of electrodes is an "active" surface, where an "active"surface is defined as a surface on which platelet aggregates build up, and wherein said second conductive region of the other of said pair of electrodes is a "non-active" surface which conducts electrical current but does not support platelet build up.

9. A platelet aggregation electrode assembly as set forth in claim 2 wherein said pair of electrodes are disposed against the same surface of said substrate, and with said substrate and insulating material form a three layer sandwich.

10. A platelet aggregation electrode assembly as set forth in claim 2 wherein said pair of electrodes are disposed against discrete opposite faces of said substrate, and with said substrate and insulating material form a five layer sandwich.

11. A platelet aggregation electrode assembly as set forth in claim 2 wherein the said total sandwich thickness is in the range substantially between 0.005 inches and 0.025 inches.

12. A platelet aggregation electrode assembly as set forth in claim 2 wherein said substrate is a substantially planar piece of plastic material.

13. A platelet aggregation electrode assembly as set forth in claim 2 wherein said second conductive region of at least one of said pair of electrodes is an "active" surface, where an "active" surface is defined as a surface on which platelet aggregates build up.

14. A platelet aggregation electrode assembly as set forth in claim 2 wherein said second conductive regions of both of said pair of electrodes are "active" surfaces, where an "active" surface is defined as a surface on which platelet aggregates build up.

15. A platelet aggregation electrode assembly as set forth in claim 2 wherein said second conductive region of one of said pair of electrodes is an "active" surface, where an "active" surface is defined as a surface on which platelet aggregates build up, and wherein said second conductive region of the other of said pair of electrodes is a "non-active" surface which conducts electrical current but does not support platelet build up.

16. A platelet aggregation electrode assembly as set forth in claim 2 wherein the area of said second conductive region of one of said pair of electrodes is much smaller than the area of said second conductive region of the other of said pair of electrodes.

17. A platelet aggregation electrode assembly as set forth in claim 2 wherein the said second conductive region of one of said pair of electrodes is disposed in a plane including said thickness dimension, and wherein the said second conductive region of the other of said pair of electrodes is disposed in a plane not including said thickness dimension.

18. A platelet aggregation electrode assembly as set forth in claim 2 wherein the said second conductive region of each of said pair of electrodes is disposed in a plane including said thickness dimension.

19. A platelet aggregation electrode assembly as set forth in claim 2 wherein the said second conductive region of at least one of said pair of electrodes is at least partially disposed in a plane including said thickness dimension.

20. A platelet aggregation electrode assembly comprising in combination,
  (a) an electrically non-conductive and blood non-reactive substrate for supporting a pair of electrodes, said substrate being a substantially planar piece of plastic material,
  (b) a pair of first and second electrically conductive spaced apart electrodes adhered to and extending for a distance along at least one surface of said substrate, said electrodes each having a first conductive region for electrical connection to a measuring circuit, and each having a second conductive region for immersion in a platelet carrying medium, said first and second conductive regions of each electrode being spaced apart from each other by an intervening length of each said electrode,
  (c) a layer of electrical insulating material entirely overlying each of said pair of electrodes except at said first and second conductive regions of each said electrode,
  (d) said substrate, said electrodes and said insulating material forming a three dimensional sandwich structure having a total thickness dimension in the range substantially between 0.005 inches and 0.025 inches, said thickness dimension being small compared to its other two dimensions, and
  (e) said second conductive region of at least one of said pair of electrodes being at least partially disposed in a plane including said thickness dimension.

* * * * *